United States Patent [19]
Arhancet et al.

[11] Patent Number: 5,416,258
[45] Date of Patent: May 16, 1995

[54] METHODS FOR INHIBITING ETHYLENICALLY UNSATURATED MONOMERS

[75] Inventors: Graciela B. Arhancet, Katy; Paul V. Roling, Spring, both of Tex.

[73] Assignee: Betz Laboratories, Inc., Trevose, Pa.

[21] Appl. No.: 182,813

[22] Filed: Jan. 14, 1994

[51] Int. Cl.$^6$ ................................ C07C 7/20
[52] U.S. Cl. ........................ 585/3; 585/5; 585/601
[58] Field of Search ................ 585/3, 5, 601

[56] References Cited

U.S. PATENT DOCUMENTS

| | | | |
|---|---|---|---|
| 4,929,778 | 5/1990 | Roling | 585/3 |
| 5,043,504 | 8/1991 | Bedell | 585/3 |
| 5,345,030 | 9/1994 | Sun et al. | 585/369 |

FOREIGN PATENT DOCUMENTS

| | | | |
|---|---|---|---|
| 0240297 | 10/1987 | European Pat. Off. | 585/3 |
| 0120521 | 9/1980 | Japan . | |
| 0763313 | 9/1980 | U.S.S.R. . | |
| 1098200 | 5/1986 | U.S.S.R. . | |

OTHER PUBLICATIONS

Taimr & Pospisil,1 "An Investigation of the Synergism between N-isopropyl-N'-phenyl-1, 4-phenylenediamine and 2,6-dialkylphenols," *Antioxidants and Stabilizers*, 98 (1984), pp. 181-188.

Taimr & Pospisil, "A Cooperative Effect between Antioxidants N-isopropyl-N'-phenyl-1,4-phenylene diamine and 2,6-di-tert-butylphenol," *Polymer Degradation and Stability*, 8 (1984), pp. 23-35.

*Primary Examiner*—Anthony McFarlane
*Attorney, Agent, or Firm*—Alexander D. Ricci; Richard A. Paikoff

[57] ABSTRACT

Methods and compositions are provided for inhibiting the polymerization of butadiene-containing streams during elevated temperature processing thereof or during storage or shipment of monomer containing product. The composition comprises a combination of (a) a phenylenediamine compound having at least one N—H bond and (b) a hydroxytoluene compound. The methods comprise adding from about 1–250 ppm of the combination to the monomer medium, per one million parts of medium.

13 Claims, No Drawings

METHODS FOR INHIBITING ETHYLENICALLY UNSATURATED MONOMERS

FIELD OF THE INVENTION

The present invention pertains to methods for inhibiting the undesired polymerization of butadiene and butadiene-containing streams, during processes such as monomer preparation and purification, and during storage and shipment of products containing butadiene.

BACKGROUND OF THE INVENTION

It is well known that butadiene readily polymerizes when heated. Heat polymerization is rapid. In fact, polymerization increases with increasing temperature. This polymerization is undesirable during many stages of the manufacturing, processing, handling, storage and use of butadiene.

The common industrial method for producing butadiene includes a variety of purification processes, including distillation, to remove impurities. Unfortunately, purification operations carried out at elevated temperatures result in an increased rate of undesired polymerization. Polymerization, such as thermal polymerization, during the monomer purification process, results in loss of production efficiency caused by polymer formation and in agglomeration on process equipment. In heat requiring operations, such agglomeration adversely affects heat transfer efficiency.

PRIOR ART

Russian Patent 1,098,200 teaches the use of aromatic amines in combination with phenols to inhibit polymerization of only isoprene, used in synthetic rubber production. This work was performed in air and with 10,000 ppm of total inhibitors at 100° C.

DETAILED DESCRIPTION OF THE PREFERRED EMBODIMENT

In accordance with the invention both a phenylenediamine compound and a hydroxytoluene compound are conjointly utilized to inhibit polymerization of butadiene and butadiene-containing streams. By butadiene-containing streams. It is meant streams containing butadiene in at least about 10 weight percent to about 100 weight percent. The experimental and field environments of the present invention have atmospheres that are low in oxygen about 10 ppm or less.

As to the phenylenediamines that may be used, these include the phenylenediamines having at least one N—H bond. It is thought that o-phenylenediamine or derivatives thereof having at least one N—H bond are suitable in accordance with the instant invention.

However, the preferred phenylenediamines are the p-phenylenediamines having the structure:

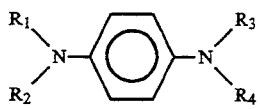

wherein $R_1$, $R_2$, $R_3$ and $R_4$ are the same or different and are hydrogen, alkyl, aryl, alkaryl, or aralkyl groups with the proviso that at least one of $R_1$, $R_2$, $R_3$ or $R_4$ is hydrogen. More preferably, the alkyl, aryl, alkaryl, and aralkyl groups have one to about twenty carbon atoms. The alkyl, aryl, alkaryl and aralkyl groups may be straight or branched-chain groups. Exemplary p-phenylenediamines include p-phenylenediamine wherein $R_1$, $R_2$, $R_3$ and $R_4$ are hydrogen; N-phenyl-N-alkyl-p-phenylenediamines such as, N-phenyl-N'-methyl-p-phenylenediamine, N-phenyl-N'-ethyl-p-phenylenediamine, N-phenyl-N'-n-propyl-p-phenylenediamine, N-phenyl-N'-isopropyl-p-phenylenediamine, N-phenyl-N'-n-butyl-pphenylenediamine, N-phenyl-N'-isobutyl-p-phenylenediamine, N-phenyl-N'-sec-butyl-p-phenylenediamine, N-phenyl-N'-tert-butyl-p-phenylenediamine, N-phenyl-N'-n-pentyl-p-phenylenediamine, N-phenyl-N'-n-hexyl-p-phenylenediamine, N-phenyl-N'-(1-methylhexyl)-p-phenylenediamine, N-phenyl-N'-(1,3-dimethylbutyl)-p-phenylenediamine, N-phenyl-N'-(1,4-dimethylpentyl)-p-phenylenediamine, N-phenyl-N', N'-dialkyl-p-phenylenediamines such as, N-phenyl-N', N-dimethyl-p-phenylene-diamine, N-phenyl-N', N'-diethyl-p-phenylenediamine, N-phenyl-N', N'-di-n-butyl-p-phenylenediamine, N-phenyl-N'-N'-di-sec-butyl-p-phenylenediamine, N-phenyl-N'-methyl-N'-ethyl-p-phenylenediamine; N,N-dialkyl-pphenylenediamines such as N,N-dimethyl-p-phenylenediamine, and N,N-diethyl-p-phenylenediamine; N,N'-dialkyl-p-phenylenediamines such as N,N'-dimethyl-p-phenylenediamine, N,N'-diethyl-p-phenylenediamine, and N,N'-di-isopropyl-p-phenylenediamine; N,N'-diaryl-p-phenylenediamines such as N,N'-diphenyl-p-phenylenediamine; N,N,N'-trialkyl-pphenylenediamines such as N,N,N'-trimethyl-p-phenylenediamine, and N,N,N'-triethyl-p-phenylenediamine. Preferably, the p-phenylenediamine is selected from the group consisting of N-phenyl-N'-(1,3-dimethylbutyl)-p-phenylenediamine, N-phenyl-N'-(1,4-dimethylpentyl)-p-phenylenediamine and N,N'-bis(sec-butyl)-p-phenylenediamine.

The total amount of phenylenediamine or derivatives thereof having at least one N—H group and hydroxytoluene compound used in the methods of the present invention as a polymerization inhibitor is that amount which is sufficient to affect inhibition of polymerization and will vary according to the conditions under which the monomer is synthesized, processed, and/or stored. At higher temperatures, larger amounts of the antipolymerization treatment are generally required. Preferably, the total amount of combined treatment (i.e., phenylenediamine or derivative thereof having at least one N—H group and hydroxytoluene) is from about 1 ppm to about 250 ppm combined treatment based on the weight of the monomer. Most preferably, the total amount of the aforesaid compounds is from 1 ppm to about 100 ppm based on the weight of the monomer. The weight ratios of phenylenediamine or derivatives thereof having at least one N—H group to hydroxytoluene are preferably in the range of about 3:1 to about 1:3. Most preferably, the weight ratio of phenylenediamine or derivative thereof having at least one N—H group to hydroxytoluene is about 1:1.

The method of the present invention can control the fouling of processing equipment, such as the equipment used in separation and purification processes of butadiene, which is due to or caused by the polymerization of the monomer. The instant invention may be used as a process inhibitor, which is employed during processing (e.g., employing heat) of the monomer. The phenylenediamine or derivative thereof having at least one N—H group and hydroxytoluene can be added to the monomer by any conventional method. The components can be added to the monomer as a single composition containing the inhibitor compounds or the individual components can be added separately or in any other desired combination. The composition can be added as either a dispersion or as a solution using a suitable liquid carrier dispersing medium or solvent which is compatible with the monomer. Preferably, a solution is provided and the solvent is a non-polar organic solvent such as xylene (a commercial mixture of o, m, and p isomers), or heavy aromatic naphtha.

Based upon presently available data, the composition preferred for use is N-phenyl-N'-(1,4-dimethylpentyl)-p-phenylenediamine and 2,6-di-tert-butyl-para-cresol (butylated hydroxytoluene, or BHT) in a 1:1 weight ratio dissolved in heavy aromatic naphtha.

The data set forth below were developed and demonstrate the unexpected results occasioned by use of the invention. The following examples are included as being illustrations of the invention and should not be construed as limiting the scope thereof.

Isoprene was used as a model for butadiene because of handling ease (isoprene boils at 34° C. vs. −4° C. for butadiene).

The inhibitor composition was tested under the heat induced gum test. 10 ml of distilled isoprene was dissolved in 40 ml of heptane, placed in a test bomb, and the appropriate treatment was added. The bomb was pressurized twice to 100 psig with nitrogen and the pressure released. The solution was heated at 100° C. under 100 psig of nitrogen, for 4 hours. The liquid was then evaporated and the remaining gum was weighed. In another experiment, the solution was purged with argon for 10 minutes prior to heating. Results are summarized in Table 1.

TABLE I

| Heat Induced Gum Test for Isoprene | | | |
|---|---|---|---|
| Treatment | ppm | mg of gums | % protection |
| Blank | — | 202 | |
| PDA/BHT (1:1) | 50/50 | 3 | 98.5 |
| PDA/BHT (1:1) | 25/25 | 2 | 99 |
| Blank | — | 222 | |
| BHT | 25 | 197 | 12 |
| PDA | 25 | 114 | 49 |
| Blank* | — | 190 | |
| PDA/.BHT* (1:1) | 50/50 | 3 | 98 |

PDA = N-phenyl-N'-(1,4-dimethylpentyl)-p-phenylenediamine
*solution purged with argon for 10 min.

The concentration of oxygen was measured with an Orbisphere membrane, before and after purging with argon. The solubility of oxygen in heptane at 1 atm and 30° C. is reported to be 45 ppm. Based on this value, the test sample contained less than 10 ppm of oxygen dissolved.

A modified test, in which 5 ml of isoprene in 45 ml of heptane were heated to 196° C., was also carried out. Results are shown in Table II.

TABLE II

| Heat Induced Gum Test for Isoprene | | | |
|---|---|---|---|
| Treatment | ppm | mg of gums (washed) | % protection |
| Heated for 15 hours | | | |
| Blank | — | 254 | |
| PDA | 500 | 154 | 39 |
| BHT | 500 | 195 | 33 |
| PDA/BHT | 1000 | 103 | 59 |
| Blank | — | 156 | |
| PDA | 500 | 145 | 7 |

TABLE II-continued

| Heat Induced Gum Test for Isoprene | | | |
|---|---|---|---|
| Treatment | ppm | mg of gums (washed) | % protection |
| BHT | 500 | 180 | none |
| PDA/BHT | 1000 | 106 | 32 |
| Heated for 18 hours | | | |
| Blank | — | 123 | |
| PDA | 500 | 132 | none |
| PDA/BHT | 1000 | 118 | 4 |
| Blank* | — | 88 | |
| PDA* | 500 | 97 | none |
| PDA/BHT* | 1000 | 75 | 15 |

*solution purged with argon for 10 min.

Additional test results are found in Tables III-V.

TABLE III

| Heat Induced Gum Tests at 100° C. for 4 hours with Isoprene | | |
|---|---|---|
| Treatment | ppm | mg of gums |
| Blank | — | 111 |
| PDA/BHT | 15/15 | 29 |
| PDA/BHT | 25/25 | 0.2 |
| PDA2/BHT | 15/15 | 0.0 |
| PDA2/BHT | 25/25 | 0.0 |

PDA = N-phenyl-N'-(1,4-dimethylpentyl)-p-phenylenediamine
PDA2 = N,N'-bis(sec-butyl)-p-phenylenediamine

TABLE IV

| Heat Induced Gum Tests at 118° C. for 2 hours with Isoprene | | |
|---|---|---|
| Treatment | ppm | mg of gums |
| Blank | — | 166, 161, 164 |
| PDA | 25 | 88 |
| PDA/BHT | 25/25 | 67, 63, 66 |
| PDA2 | 25 | 65 |
| PDA2/BHT | 25/25 | 23, 20 |
| BHT | 25 | 115 |

TABLE V

| Heat Induced Gum Tests at 100° C. for 4 hours with Isoprene | | |
|---|---|---|
| Treatment | ppm | mg of gums |
| Blank | — | 108 |
| PDA3 | 10 | 44 |
| PDA3/BHT | 10/10 | 18 |
| BHT | 10 | 122 |

PDA3 = mixture of N-phenyl-N'-(1,4-dimethylpentyl)-p-phenylenediamine and N-phenyl-N'-(1,3-dimethylbutyl)-p-phenylenediamine.

DISCUSSION

Based upon Tables I-V, the combinations of phenylenediamine compound and BHT in accordance with the invention provide % polymer inhibition protection results that are greater than the sum of the individual component protection results at comparable treatment dosages when the range of phenylenediamine:BHT is in the range of 1:1 (by weight).

Due to the unexpected results shown by the combination of phenylenediamine and BHT, it is possible to produce a more effective monomer anti-polymerization treatment than is obtainable by the use of either individual ingredient alone when measured at comparable treatment levels. Because of the enhanced polymerization inhibiting activity of the mixture, the concentration of each of the ingredients may be lowered and the total quantity of the polymerization inhibitor required for an effective treatment at elevated temperatures may be reduced. This factor is especially important in monomer purification procedures where the obvious goal of the process is to provide high level monomer purity.

The term "elevated temperatures" as used herein means temperatures of from about 80°–250° C. that are commonly utilized during the heat treatment of butadiene-containing streams. Such heat treatment processes include distillation and sundry other procedures.

The methods and compositions of the present invention can control the fouling of processing equipment, such as equipment used in the separation and purification processes of butadiene-containing streams, which is due to or caused by the polymerization of the butadiene. The instant invention is useful as a process inhibitor, which is employed during the preparation and processing of the monomer. The invention can be utilized under normal pressure (760 mm), under super-atmospheric pressure or under reduced pressure.

The phenylenediamine or derivatives thereof and hydroxytoluene compound can be provided to the monomer by any conventional method. The components can be added to the monomer as a single composition containing the inhibitor compounds or the individual components can be added separately or in any other desired combination.

While this invention has been described with respect to particular embodiments thereof, it is apparent that numerous other forms and modifications will be obvious to those skilled in the art. The appended claims generally should be construed to cover all such obvious forms and modifications which are within the true spirit and scope of the present invention.

We claim:

1. A method of inhibiting polymerization of a butadiene-containing stream during preparation and purification of said butadiene comprising adding to the butadiene-containing stream an effective inhibiting amount of a combination of (a) a phenylenediamine compound and (b) a hydroxytoluene, said method conducted in a low oxygen atmosphere, wherein said atmosphere comprises less than about 10 ppm of oxygen.

2. The method as recited in claim 1 wherein the combination is added to the butadiene-containing stream at a temperature from about 80°–250° C.

3. The method as recited in claim 2 wherein the combination is added to the butadiene-containing stream at a temperature from about 80°–150° C.

4. The method as recited in claim 1 wherein said phenylenediamine compound (a) has the structure:

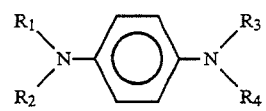

wherein $R_1$, $R_2$, $R_3$ and $R_4$ are the same or different and are hydrogen, alkyl, alkaryl, or aralkyl, with the proviso that at least one of $R_1$, $R_2$, $R_3$ or $R_4$ is hydrogen.

5. The method as recited in claim 4 wherein $R_1$, $R_2$, $R_3$ and $R_4$ each have from 1–20 carbon atoms except for at least one of $R_1$, $R_2$, $R_3$ and $R_4$ that is hydrogen.

6. The method as recited in claim 5 wherein (a) comprises N-phenyl-N'-(1,4-dimethylpentyl)-p-phenylenediamine or N,N'-bis(sec-butyl)-p-phenylenediamine.

7. The method as recited in claim 1 wherein said hydroxytoluene comprises a butylated hydroxytoluene.

8. The method as recited in claim 1 wherein the weight ratio of (a):(b) is from about 3:1 to 1:3.

9. The method as recited in claim 8 wherein said butadiene-containing stream comprises from about 10 weight percent to about 100 weight percent butadiene.

10. The method as recited in claim 9 wherein the amount of (a) and (b) added, collectively, to said butadiene is from about 1–250 ppm per one million parts of said butadiene.

11. The method as recited in claim 10 wherein the amount of (a) and (b) added, collectively, to said butadiene is from about 1–100 ppm.

12. The method as recited in claim 9 further comprising heating said butadiene.

13. The method as recited in claim 9 further comprising distilling said butadiene to remove impurities therefrom.

* * * * *